United States Patent [19]

Braschos

[11] Patent Number: 4,750,620
[45] Date of Patent: Jun. 14, 1988

[54] METHOD AND APPARATUS FOR SORTING OUT PACKAGED ITEMS IDENTIFIED AS DEFECTIVE

[76] Inventor: Karl-Heinz Braschos, Dr.-Ernst-Strasse 23, D-5900 Siegen, Fed. Rep. of Germany

[21] Appl. No.: 38,402

[22] Filed: Mar. 30, 1987

Related U.S. Application Data

[63] Continuation of Ser. No. 719,254, Apr. 2, 1985, abandoned.

[30] Foreign Application Priority Data

Jul. 3, 1984 [DE] Fed. Rep. of Germany ....... 3424360

[51] Int. Cl.⁴ ................................................ B07C 5/00
[52] U.S. Cl. .................................... 209/523; 198/372; 209/651; 209/654
[58] Field of Search ............... 209/522, 523, 651–654, 209/606; 198/367, 372, 436, 457, 467.1, 598, 722, 723

[56] References Cited

U.S. PATENT DOCUMENTS

| | | | |
|---|---|---|---|
| 2,689,647 | 9/1954 | Hofstetter et al. | 209/529 |
| 3,710,937 | 1/1973 | Cook | 198/598 |
| 4,320,840 | 3/1982 | Braschos | 209/652 |
| 4,564,105 | 1/1986 | Brouwer et al. | 198/598 |

FOREIGN PATENT DOCUMENTS

| | | | |
|---|---|---|---|
| 581773 | 7/1931 | Fed. Rep. of Germany | 198/436 |
| 1080483 | 4/1960 | Fed. Rep. of Germany | . |
| 55599 | 4/1967 | Fed. Rep. of Germany | . |
| 6600792 | 1/1969 | Fed. Rep. of Germany | . |
| 3110883 | 10/1982 | Fed. Rep. of Germany | . |
| 401608 | 10/1973 | U.S.S.R. | 198/372 |
| 664888 | 5/1979 | U.S.S.R. | 198/598 |

Primary Examiner—Robert B. Reeves
Assistant Examiner—Donald T. Hajec
Attorney, Agent, or Firm—Young & Thompson

[57] ABSTRACT

The apparatus (1) for sorting out packaged items identified as defective, especially bottles (2), by diverting same from a first horizontal conveyor belt (4) to a second conveyor belt (8) traveling beside the first belt in synchronism in parallel thereto, is characterized by a diverter (5) which is controlled in a timed fashion by an identification station (3) for defective bottles and imparts to the bottle a kinetic impulse transversely to the belt traveling direction (a). The diverter (5) comprises a motor drivable shaft (9) with a spiral coil segment (10) ascending in the belt traveling direction (a).

3 Claims, 1 Drawing Sheet

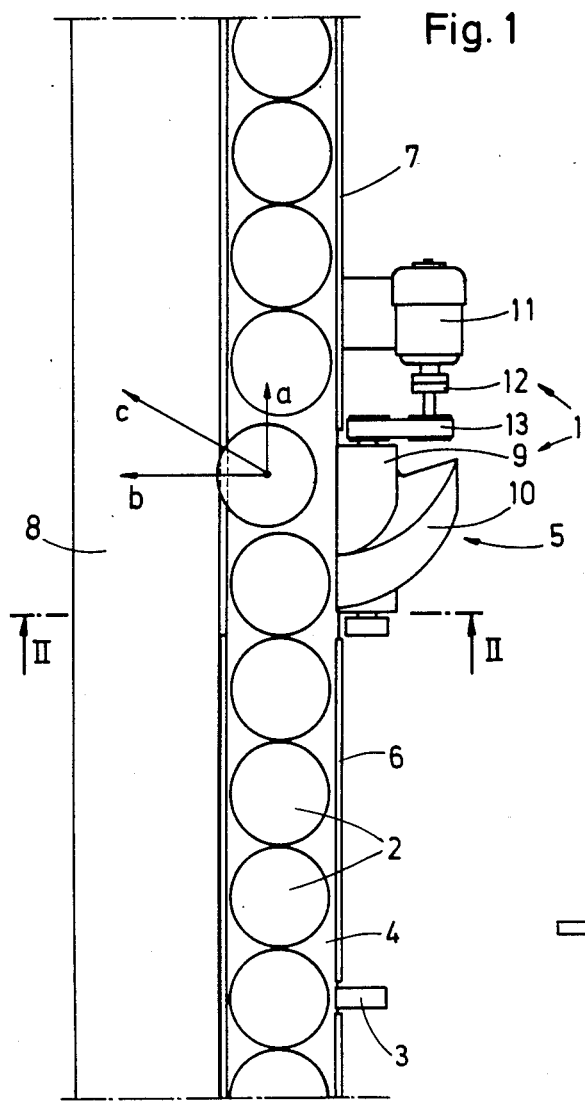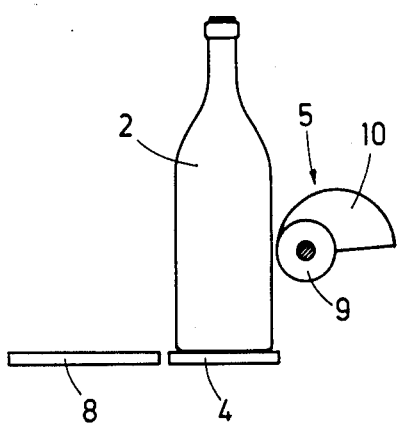

METHOD AND APPARATUS FOR SORTING OUT PACKAGED ITEMS IDENTIFIED AS DEFECTIVE

This application is a continuation of application Ser. No. 719,254, filed Apr. 2, 1985, now abandoned.

BACKGROUND OF THE INVENTION

1. Field of the Invention

The invention relates to sorting out packaged items identified as defective.

2. Description fo the Related Art

U.S. Pat. No. 2,689,647 describes a sorting-out device of this type wherein the diversion means, imparting to a bottle to be sorted out a kinetic impulse transversely to the conveying direction, is designed as a plunger exhibiting at its free end a shoe adapted to the external contour of the bottle. The kinematics of the plunger moving transversely to the conveying direction of the bottles causes a rebounding effect with an impact or striking stress being exerted on the bottle to be sorted out; such stress permits, to avoid disturbances by bottles falling over during the ejection step, merely relatively low operating speeds of the bottle processing machines, e.g. a dispensing machine or a labeling machine, connected to such a pusher sorting-out device in combination with a testing unit.

The sorting-out device according to German Patent 3,110,883 brought decisive improvement with respect to operating speed and operating safety of the aforedescribed pusher sorting-out device; in this patent, the diversion means is fashioned as a plunger exhibiting at the free end at least one roller rotatably mounted about a perpendicular axis and provided with a peripheral hoop of foam rubber or the like. The roller, in the rest position, projects by a small degree into the conveying path of the packaged items, preferably bottles. By means of this sorting-out device, the bottles, during the ejection process, are only slightly braked and accordingly do not experience practically any relative movement in the conveying direction with respect to the conveyor belt. Due to this mode of operation, the bottles can be transported past the sorting-out device on the conveyor belt without spacings, and bottle dispensing plants equipped with such a sorting-out device in combination with a corresponding testing unit attain high production efficiencies. The disadvantage of this conventional installation is to be seen in that the roller with foam rubber lining and the roller bearing at the free end of the plunger must be exchanged at regular intervals on account of the wear and tear and contamination that occur.

SUMMARY OF THE INVENTION

The invention provides a sorting out method and apparatus of the type discussed, which is distinguished by high speed and a simple construction with a low number of wear-resistant components that are safe in operation.

BRIEF DESCRIPTION OF THE DRAWING

The invention will be described in detail below with reference to an embodiment illustrated in the drawing wherein:

FIG. 1 is a schematic top view of the sortingout apparatus of this invention and FIG. 2 is a section along line II—II in FIG. 1.

DETAILED DESCRIPTION OF THE INVENTION

The apparatus 1 according to FIG. 1 for sorting out, for example, bottles 2 which have not been properly filled, is controlled by a filling level control device 3 arranged, for example, downstream of a dispensing machine, not shown. The filled bottles 2 are transported by means of a conveyor belt 4 in the direction of arrow a from the filling machine to the filling level control device 3 and from there to the sorting-out device 1. Guard railings 6, 7 ensure that the bottles 2 of the stream of bottles arrive in alignment at the diversion means 5 of the sorting-out device 1. The diversion means 5 pushes the improperly filled bottles over to a second conveyor belt 8 extending directly beside the first conveyor belt 4 in parallel thereto and being normally driven at the same speed.

The deflecting means 5 of the sorting-out device 1 comprises a motor-drivable shaft 9 with a spiral coil segment 10 ascending in the belt traveling direction a and extending over an angle of rotation of approximately 180°. The drive shaft 9 is arranged outside of the path of motion of the bottles 2 and in parallel to the conveyor belts 4, 8. The drive shaft 9 and the spiral coil segment 10 of the sorting-out device 1 are fashioned integrally and preferably consist of a synthetic resin.

The shaft 9 with the spiral coil segment 10 of the sorting-out device 1 is driven by an electric motor 11 via a clutch 12 that can be activated by the filling level control device 3 and via a toothed belt 13.

The mode of operation of the sorting-out apparatus is as follows:

In the rest position, the spiral coil segment 10 of the drive shaft 9 is disposed outside of the path of movement of the bottles 2. Upon identification of a flawed bottle by the filling level control unit 3, the clutch 12 is engaged by a control pulse from the control device at the moment that the defective bottle arrives at the spiral coil segment 10. The clutch 12 couples the drive shaft 9, together with the spiral coil segment 10 of the sorting device 1, with the electric motor 11 per control pulse for execution of a revolution; the electric motor runs with constant operation. The revolution of the spiral coil segment 10 effects a pushing over of the bottle 2 recognized as being defective from the first conveyor belt 4 to the sorting-out belt 8. The speed of rotation of the spiral coil segment 10 is adapted to the traveling speed of conveyor belt 4 so that the point of attack and/or surface of attack with which the spiral coil segment 10 comes in contact with the bottle to be sorted out will move along with the bottle in synchronism; the bottle executes a pushing-over movement in the direction of arrow c resulting from the motion component a of the conveyor belt 4 and the transverse motion component b induced by the spiral coil segment 10.

The pushing over of the defective bottles to the sorting-out belt takes place with the spiral coil segment over a time period of milliseconds whereby substantially more favorable force transmission relationships arise between the diversion means and the bottle than in the conventional sorting-out devices which push the flawed bottles over in a single instant by means of a plunger. This kinematic behavior of the sorting-out device 1 permits a sorting out that is safe in operation for defective bottles in bottle processing plants with washing installations, dispensing and labeling machines, which can be operated at high processing capacities of up to 90,000 units per hour.

It will thus be seen that the present invention provides improved apparatus for sorting out containers, of the type in which defective containers are selectively diverted from a flat horizontal conveyor belt while leaving on the belt containers that are not defective, utilizing diversion means imparting to the defective containers a kinetic impulse transversely to the belt. The particular improvement provided by the present invention comprises diversion means 5 in the form of a motor-drivable shaft 9 parallel to and disposed above the flat horizontal conveyor belt and spaced to one side of the containers moving on the conveyor belt, the shaft 9 having a spiral segment 10 thereon that contacts defective containers on the belt. Spiral segment 10 imparts a horizontal thrust to the contacted containers to diver the contacted containers from the conveyor belt. To this end, spiral segment 10 contacts the containers at a point intermediate the height of the containers; and spiral segment 10 at this point of contact moves downward. A second flat horizontal conveyor belt 8 is disposed beside and parallel to and coplanar with the first-mentioned belt; and the contacted containers are diverted by spiral segment 10 from the first belt 4 to the second belt 8.

What is claimed is:

1. A method for sorting out defective containers, identified as such by an identification station, from non-defective containers, said defective containers being selectively diverted from non-defective containers by a diversion means as the containers travel in a conveying direction on a flat horizontal conveyor belt, said diversion means imparting to the defective containers a kinetic impulse transversely to said conveying direction; the improvement comprising providing said diversion means with a rotatable spiral segment for contacting a container on the belt, said spiral segment being rotatable about a horizontal axis parallel to and disposed above and spaced to one side of the belt, said spiral segment imparting a horizontal thrust to the contacted containers to divert the contacted containers from said conveyor belt, said spiral segment contacting the containers at a point intermediate the height of the containers, and said spiral segment at said point of contact moving downward.

2. (amended) An apparatus for sorting out defective containers, identified as such by an identification station, from non-defective containers, said defective containers being selectively diverted from non-defective containers by a diversion means as the containers travel in a conveying direction on a flat horizontal conveyor belt, said diversion means imparting to the defective containers a kinetic impulse transversely to said conveying direction; the improvement in which the diversion means (5) comprises a motor-drivable shaft (9) parallel to and disposed above the flat horizontal conveyor belt and spaced to one side of the containers moving on said conveyor belt, said shaft (9) having a spiral segment (10) thereon that contacts defective containers on the belt, said spiral segment imparting a horizontal thrust to the contacted containers to divert the contacted containers from said conveyor belt, said spiral segment contacting the containers at a point intermediate the height of the containers, and said spiral segment (10) at said point of contact moving downward.

3. Apparatus as claimed in claim 2, and a second flat horizontal conveyor belt beside and parallel to and coplanar with the first-mentioned belt, onto which the contacted containers are diverted by said spiral segment from the first-mentioned belt.

* * * * *